United States Patent [19]
Abrahams

[11] Patent Number: 5,373,743
[45] Date of Patent: Dec. 20, 1994

[54] BACKSPLASH PROTECTION FOR ULTRASONIC INSPECTION SYSTEM

[75] Inventor: John W. Abrahams, Smyrna, Tenn.
[73] Assignee: Avco Corporation, Providence, R.I.
[21] Appl. No.: 90,504
[22] Filed: Jul. 12, 1993
[51] Int. Cl.$^5$ .................. G01N 29/06; G01N 29/28
[52] U.S. Cl. .................................................. 73/644
[58] Field of Search .................. 73/624, 625, 627, 628, 73/629, 644

[56] References Cited

U.S. PATENT DOCUMENTS

| | | | |
|---|---|---|---|
| 2,751,783 | 6/1956 | Erdman | 73/67 |
| 3,121,325 | 2/1964 | Rankin et al. | 73/67.7 |
| 3,122,661 | 2/1964 | Joy | 310/8.7 |
| 3,255,626 | 6/1966 | Van Der Veer | 73/71.5 |
| 3,420,097 | 1/1969 | Battermann et al. | 73/71.5 |
| 3,555,891 | 1/1971 | Lewis | 73/71.5 |
| 3,662,590 | 5/1972 | Shiraiwa et al. | 73/71.5 |
| 3,745,833 | 7/1973 | Armstrong | 73/67.8 R |
| 4,558,598 | 12/1985 | Young | 73/644 |
| 4,726,231 | 2/1988 | Tretout et al. | 73/644 |
| 4,976,149 | 12/1990 | Ichikawa et al. | 73/644 |

FOREIGN PATENT DOCUMENTS

| | | |
|---|---|---|
| 1275693 | 1/1960 | France . |
| 46-8391 | 3/1971 | Japan . |

*Primary Examiner*—Hezron E. Williams
*Assistant Examiner*—Rose M. Finley
*Attorney, Agent, or Firm*—Perman & Green

[57] ABSTRACT

A gas jet is positioned above the water nozzle of a system provided for ultrasonically detecting flaws in an article to be inspected. The water nozzle directs a substantially level water jet stream against an upright surface of the article as it is moved transversely of the nozzle. A transducer associated with the water nozzle transmits ultrasonic energy along the water jet stream toward the article, then receives echoes from flaws existing in the article. The gas jet directs toward the upright surface of the article a gas jet stream which is substantially parallel to, and vertically aligned with, the water jet stream. The gas jet stream serves to deflect the water splashing off the surface of the article after impact therewith and prevents the splashing water from descending toward and striking the water jet stream. The water nozzle and the gas jet may be positioned such that the longitudinal axes of the water jet stream and of the gas jet stream are both substantially perpendicular to the surface of the article being inspected. Preferably, the water jet stream exhibits laminar flow. Signals may be recorded which are received from the transducer representative of the attenuation of the ultrasonic energy caused by the condition of the article being inspected. In a further embodiment, opposed systems, each comprised of a water nozzle, gas jet, and associated transducer, may be positioned to direct water jet and gas jet streams against the article from opposite sides of the article, the opposed water jet and gas jet streams being substantially parallel and vertically aligned.

15 Claims, 2 Drawing Sheets

BACKSPLASH PROTECTION FOR ULTRASONIC INSPECTION SYSTEM

BACKGROUND OF THE INVENTION

The present invention relates generally to ultrasonic testing of articles and, more particularly, to apparatus providing relief against backsplash resulting when the laminar flow water column used for transmitting the ultrasonic waves creates a cascading waterfall after striking the article being tested and impairs the quality of the water column.

II. Description of the Prior Art

It has long been known to perform nondestructive inspection employing ultrasonic waves travelling between a transducer and the article being inspected. Since liquids are a good media for transmitting this wave energy, it has been customary in the past to submerge the transducer or transducers and the object to be inspected, or at least part of the object to be inspected, in the liquid medium. This system worked as long as the object being inspected was not too large. However, it was completely impractical when the object being inspected was of substantial size such as, for example, large sheets or plates.

For such large objects, it heretofore became the practice to mount the transducer in a suitably shaped container which had an opening shaped to closely match the contour of the object and, by keeping the container filled with liquid, to attempt to maintain a fluid seal sufficient to keep the container full and a liquid coupling between the transducer and the object. This method had the inherent disadvantage of requiring a close fit between the edges of the container and the surface of the object being inspected which made it impossible to accommodate large surface defects and protrusions such as weld beads, gouges, or changes in contour, without losing the liquid coupling. Since a break in the fluid connection between the transducer and the article interrupts the inspection process, this method proved to be unsatisfactory.

Another method sometimes suggested for coupling the transducer to the article employs a housing for the transducer which has an outlet equipped with a nozzle. The liquid is introduced into the housing under pressure so that it is expelled through the nozzle toward the surface of the object as a high velocity, uncontained, stream or jet of liquid. The transducer is located in the housing so that the ultrasonic waves can travel to the article through this high velocity stream of liquid. In more recent versions of this method, a pair of aligned transducers with their associated nozzles are positioned on opposite sides of a large plate or other object to be inspected. This has generally come to be a very satisfactory ultrasonic inspection method.

In order to more clearly define the evolution of ultrasonic inspection techniques and the existing state of the art in this regard, a number of specific prior art disclosures will here be mentioned. For example, U.S. Pat. Nos. 3,662,590 issued May 16, 1971 to Shiraiwa, No. 3,555,891 issued Jan. 19, 1971 to Lewis, and No. 3,255,626 issued Jun. 14, 1966 to Van Der Veer all broadly disclose ultrasonic inspection apparatus. U.S. Pat. No. 3,121,325 issued Feb. 18, 1964 to Rankin et al. discloses the use of air jets from a manifold to keep the top surfaces of ultrasonic probes free of the coupling water. U.S. Pat. Nos. 3,122,661 issued Feb. 25, 1964 to Joy and 3,420,097 issued Jan. 7, 1969 to Battermann et al., disclose the use of air jets in combination with ultrasonic inspection devices to confine the coupling fluid to a desired area. U.S. Pat. No. 3,745,833 issued Jul. 17, 1973 to Armstrong and French Patent No. 1,275,693 issued Nov. 2,1961 to U.K Atomic Energy Authority both disclose the use of air jets in combination with ultrasonic inspection devices to deflect the coupling water stream. U.S. Pat. No. 2,751,783 issued Jun. 26, 1956 to Erdman and Japanese Disclosure No. 46-8391 dated Aug. 2,1967 to Mitsubishi Juko disclose, respectively, a splash box and a shield for containing the coupling water stream used in an ultrasonic inspection device.

SUMMARY OF THE INVENTION

It was with knowledge of the state of the art as noted above that the present invention was conceived and has now been reduced to practice. According to the present invention, a gas jet is positioned above the water nozzle of a system provided for ultrasonically detecting flaws in an article to be inspected. The water nozzle directs a substantially level water jet stream against an upright surface of the article as it is moved transversely of the nozzle. A transducer associated with the water nozzle transmits ultrasonic energy along the water jet stream toward the article, then receives echoes from flaws existing in the article. The gas jet directs toward the upright surface of the article a gas jet stream which is substantially parallel to, and vertically aligned with, the water jet stream. The gas jet stream serves to deflect the water splashing off the surface of the article after impact therewith and prevents the splashing water from descending toward and striking the water jet stream. The water nozzle and the gas jet may be positioned such that the longitudinal axes of the water jet stream and of the gas jet stream are both substantially perpendicular to the surface of the article being inspected. Preferably, the water jet stream exhibits laminar flow. Signals may be recorded which are received from the transducer representative of the attenuation of the ultrasonic energy caused by the condition of the article being inspected. In a further embodiment, opposed systems, each comprised of a water nozzle, gas jet, and associated transducer, may be positioned to direct water jet and gas jet streams against the article from opposite sides of the article, the opposed water jet and gas jet streams being substantially parallel and vertically aligned.

A primary object of the invention, therefore, is to provide an improved system for ultrasonically detecting flaws in an article which utilizes a water jet stream directed against a surface of the article as the medium for transmission of an ultrasonic signal. Another object of the invention is to provide such a system which operates to deflect the water splashing off the article away from interfering with the water jet stream.

A further object of the invention is to provide such a system which utilizes an air jet stream positioned above the water jet stream to deflect the water splashing off the surface of the article and prevents the splashing water from descending toward and striking the water jet stream.

Yet another object of the invention is to provide such a system according to which mutually opposing water jet streams and gas jet streams are directed at the article from opposite sides of the article.

Other and further features, objects, advantages, and benefits of the invention will become apparent from the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention and, together with the description, serve to explain the principles of the invention in general terms. Like numerals refer to like parts throughout the disclosure.

DETAILED DESCRIPTION OF THE PREFERRED EMBODIMENT

Figure 1:
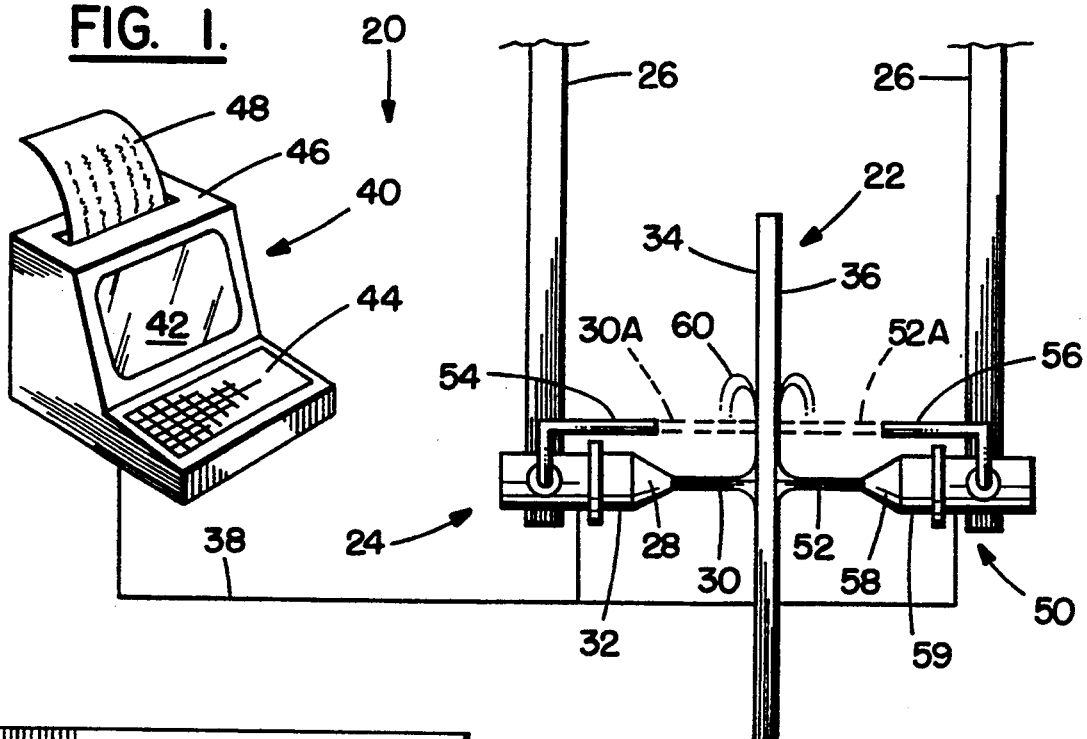
FIG. 1 is a diagrammatic view, partly in elevation and partly perspective, of an ultrasonic detection system embodying the invention.

Turn now to the drawings and, initially, to FIG. 1, which illustrates a system 20 for ultrasonically detecting flaws in an article 22 to be inspected. The article 22 may be of simple or of complex shape. Detection apparatus 24 is suitably mounted on a frame 26 such that the article 22 can be moved into or out of the plane of the paper, viewing FIG. 1. In alternative constructions, the article 22 may remain stationary and the detection apparatus 24 move into and out of the plane of the paper, or both the article and the detection apparatus may move into and out of the plane of the paper and relative to one another.

In any event, the detection apparatus 24 includes a suitable nozzle 28 which is in communication with a source of water under pressure. The nozzle 28 is capable of directing a substantially level water jet stream 30 against the article 22 as it moves transversely of the nozzle.

The detection apparatus 24 also includes a suitable transducer 32 associated with the nozzle 28 for transmitting ultrasonic energy signals along the water jet stream 30 toward a surface 34 of the article 22. Echoes from opposite surfaces 34, 36 of the article 22 as well as from internal flaws within the article 22 are the returned to the transducer 32 via the water jet stream 30. These echoes are representative of the attenuation of the initial ultrasonic energy signals and are transmitted in a known manner as schematically depicted by an electrical lead 38 to suitable computer apparatus 40. The computer apparatus may include a monitor 42 for viewing the attenuated signals, a keyboard 44 for inputting appropriate additional information, and an output device 46 such as a printer for providing a detailed printout in order to provide a lasting record of the attenuated signals portraying the condition of the article 22.

In situations wherein the article 22 is reasonably planar and has a relatively nominal thickness, a second detection device 50 including a nozzle 58 and a suitable transducer 59 may be supported on the frame 26 and located on an opposite side of the article 22 to direct a second water jet stream 52 onto the surface 36. In this instance, the water jet streams 30 and 52 are substantially aligned, or coaxial. In a preferred construction, the water jet streams 30, 52 are substantially perpendicular to the surfaces 34, 36 at which they are directed.

Figure 2:
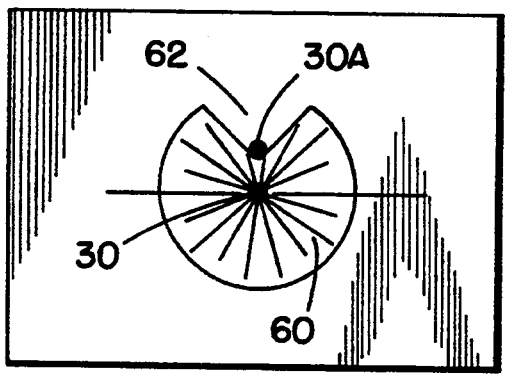
FIG. 2 is a detail perspective view of components of the invention depicted in FIG. 1 and, specifically, a water jet nozzle and an air jet nozzle directing, respectively, a water jet stream and an air jet stream against the surface of an article being inspected.

Each of the detection devices 24, 50 includes an associated gas jet 54, 56, respectively, which is suitably connected to a source of pressurized gas, such as air. The gas jets 54, 56 are positioned above their associated nozzles 28, 58 such that they direct toward their associated surfaces 34, 36 of the article 22 gas jet streams 30A and 52A, respectively. The gas jet and water jet streams are preferably parallel and generally lie in a common vertical plane. This relationship may be more clearly seen in FIG. 2.

Figure 3:
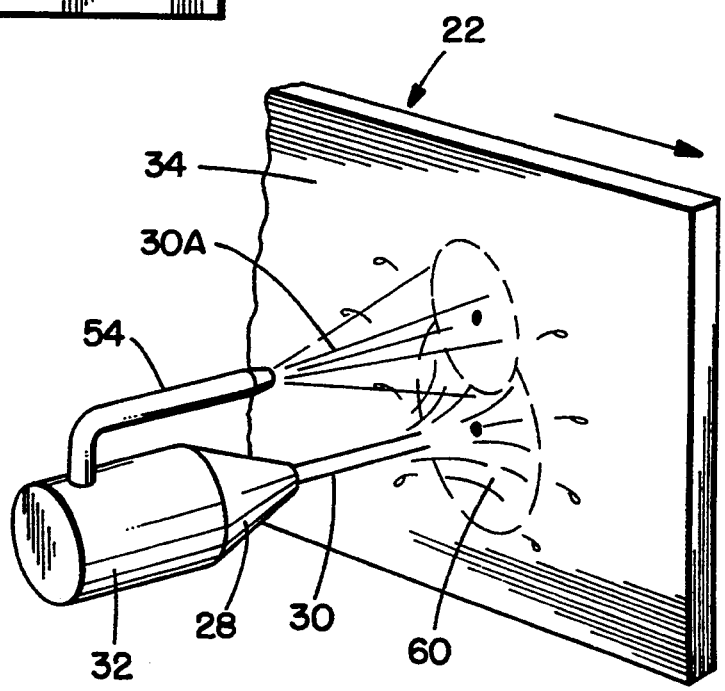
FIG. 3 is a detail elevation view of the surface of the article being inspected in FIG. 2 and depicting the resulting effect of the water jet stream and of the air jet stream thereon.

It will be appreciated that when the water jet stream 30 strikes the surface 34 of the article 22 in the absence of the gas jet stream 30A, the water forms a splash region 60 (FIGS. 1, 2 and 3) wherein water splashes in all directions and that water in the region above the water jet stream 30 often descends toward and strikes the water jet stream. This causes interference with the signals from the transducers 32, 59 as well as of the echoes returning from the article 22 and, therefore, substantially affects the information being processed by the computer apparatus 40. This has been a long known and persistent problem but has been effectively solved by means of the present invention. Specifically, the gas jet streams 30A, 52A as particularly well seen in FIG. 3 (with respect to gas jet stream 30A), provide an effective shield which prevents cascading droplets from a former splash region 62 (FIG. 3) from descending toward and striking the water jet stream 30. The gas jet stream 30A can be, but does not necessarily have to be, parallel to the water jet stream 30. The goal is to displace a significant portion of water from above the ultrasonic signals. The gas jet stream can be radially placed anywhere above the water jet stream where it is most effective and practical for that operation. It can be said in general that being parallel with the water jet stream and perpendicular to the test article is the most suitable for inspecting purposes. However, there are many arrangements, taking into account such variables as nozzle angle, distance from articles, diameter, and air pressure, that could be just as effective.

The following parameters are typical for the operation of the invention but are not presented for purposes of limiting in invention in any manner:

Average air pressure = 10 psi
Average distance from article = 1 inch
Nozzle diameter = ⅛ inch
Nozzle angle = 90 degrees to article surface 34

Figure 4:
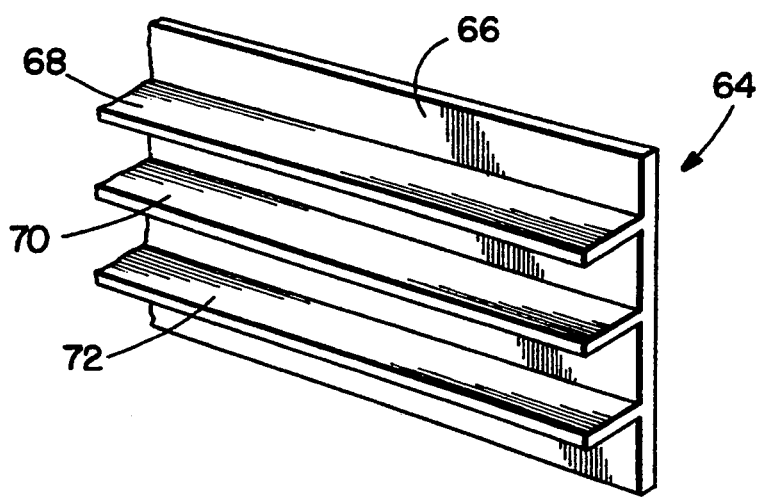
FIG. 4 is a detail perspective view, similar to FIG. 2, illustrating a water jet nozzle and an air jet nozzle directing their respective streams onto the surface of a modified article.
Figure 5:
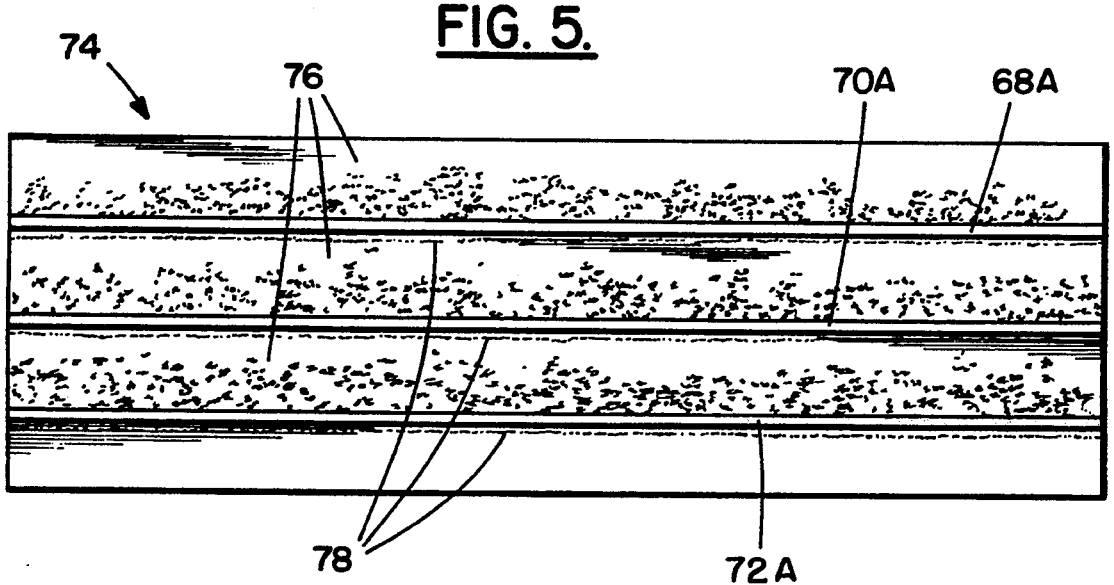
FIG. 5 is a computer output plot of an attenuated signal resulting from inspection of the modified article of FIG. 4 without operation of the air jet nozzle of the invention.

Turn now to FIG. 4 which illustrates a modified article 64 to be inspected. In this instance, the water nozzle 28 and gas jet 54 (illustrated in FIG. 2) direct their jet streams 30 and 30A, respectively, toward a surface 66 which is modified, for example, by means of a plurality of outwardly projecting blades 68, 70, 72. In FIG. 5, a computer printout 74 relates to the modified article 64 and depicts indica 68A, 70A, and 72A which represent, respectively, their associated blades 68, 70, and 72. In between the blades, there is substantial interference, or "noise" indicted by the speckled areas 76 located between the blade indicia 68A, 70A, and 72A. A linear marking 78 adjacent each of the blade indicia 68A, 70A, and 72A is common interference caused by the presence of the associated blade 68, 70, and 72 and is recognizable by the skilled person who would be viewing the computer printout 74.

Figure 6:
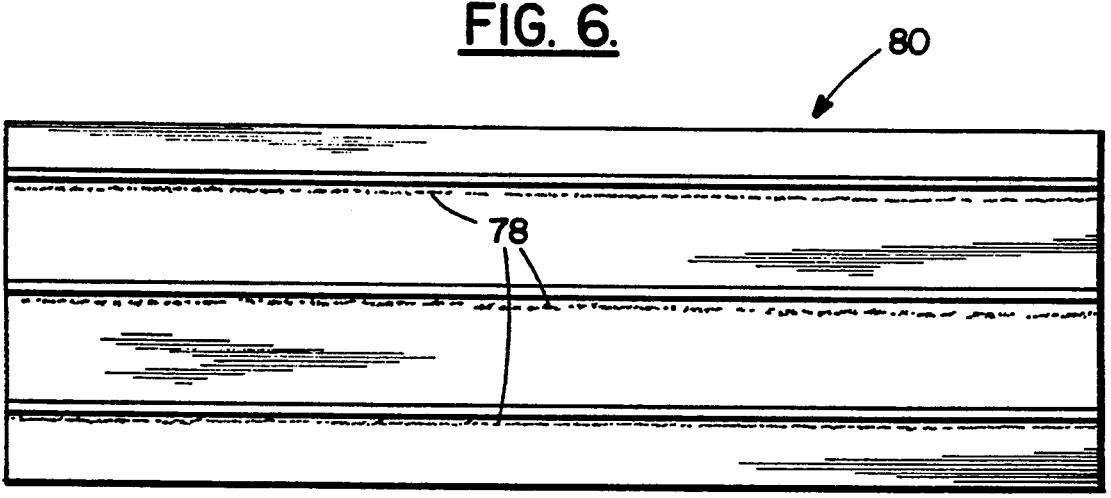
FIG. 6 is a computer output plot of an attenuated signal resulting from inspection of the modified article of FIG. 4 utilizing operation of the air jet nozzle of the invention.

FIG. 6 illustrates an improved computer printout 80 which results from operation of the gas jet 54. Unfortunately, the linear markings 78 remain. This condition is created when the blade 68 separates the gas jet stream from the water jet stream during scanning and thus backsplash cannot be avoided. However, this condition can be corrected if the gas jet is situated immediately above the water jet stream and not an inch above it, as was the case for this particular demonstration.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. Apparatus for ultrasonically detecting flaws in an article to be inspected comprising:
   nozzle means positioned to direct a substantially level water jet stream against the article as the article is moved transversely thereof;
   transducer means for transmitting ultrasonic energy along the water jet stream toward a substantially upright surface of the article to be inspected, and for receiving echoes from the surface of the article and from internal flaws within the article; and
   gas jet means positioned above said nozzle means for directing toward the upright surface of the article to be inspected a gas jet stream which is substantially parallel to the water jet stream for deflecting away from the water jet stream the water splashing off the surface of the article after impact therewith, to prevent the splashing water from descending toward and striking the water jet stream.

2. Ultrasonic detection apparatus as set forth in claim 1
   wherein said nozzle means is positioned such that the longitudinal axis of the water jet stream is substantially perpendicular to the surface of the article being inspected; and
   wherein said gas jet means is positioned such that the longitudinal axis of the gas jet stream is substantially perpendicular to the surface of the article being inspected.

3. Ultrasonic detection apparatus as set forth in claim 1
   wherein said nozzle means is adapted to emit a water jet stream exhibiting laminar flow.

4. Ultrasonic detection apparatus as set forth in claim 1 including:
   recording means for receiving signals from said transducer means representative of the echoes received by the transducer means.

5. Ultrasonic detection apparatus as set forth in claim 1 including:
   wherein said nozzle means and said gas jet means are positioned such that the water jet stream and the gas jet stream are coplanar and vertically aligned.

6. Apparatus for ultrasonically detecting flaws in an article to be inspected comprising:
   first and second nozzle means positioned to direct, respectively, substantially level first and second water jet streams against the article from opposite sides thereof as the article is moved transversely of said first and second nozzle means, the first water jet stream being substantially aligned with the second water jet stream;
   first transducer means for transmitting and receiving ultrasonic energy operatively associated with said first nozzle means;
   second transducer means for transmitting and receiving ultrasonic energy operatively associated with said second nozzle means;
   said first transducer means operable for transmitting ultrasonic energy along the first water jet stream toward a first substantially upright surface of the article to be inspected, through the article and into the second water jet stream for reception by said second transducer means, the ultrasonic energy being altered by flaws present on the surfaces of the article and internally within the article;
   said second transducer means operable for transmitting ultrasonic energy along the second water jet stream toward a second substantially upright surface of the article to be inspected, wherein said second surface is opposite said first surface and the ultrasonic energy propagates through the article and into the first water jet stream for reception by said first transducer means, the ultrasonic energy being altered by flaws present on the surfaces of the article and internally within the article; and
   first and second gas jet means positioned, respectively, above said first and second nozzle means for directing toward the upright surfaces of the article to be inspected, respectively, first and second gas jet streams which are substantially parallel to the first and second water jet streams for deflecting away from the water jet streams water splashing off the surfaces of the article after impact therewith to prevent the splashing water from descending toward and striking the water jet streams.

7. Ultrasonic detection apparatus as set forth in claim 6:
   wherein each of said first and second nozzle means is positioned such that the longitudinal axes of the first and second water jet streams are substantially perpendicular to the first and second surfaces, respectively, of the article being inspected; and
   wherein each of said first and second gas jet means is positioned such that the longitudinal axes of the first and second gas jet streams are substantially perpendicular to the first and second surfaces, respectively, of the article being inspected.

8. Ultrasonic detection apparatus as set forth in claim 6:
   wherein each of said first and second nozzle means is adapted to emit a water jet stream exhibiting laminar flow.

9. Ultrasonic detection apparatus as set forth in claim 6 including:

recording means for receiving signals from said first and second transducer means representative of the attenuation of the ultrasonic energy caused by the condition of the article being inspected.

10. Ultrasonic detection apparatus as set forth in claim 6 including:

wherein said first and second nozzle means and said first and second gas jet means are positioned such that the first and second water jet streams are coplanar and vertically aligned respectively with the first and second gas jet streams.

11. A method of ultrasonically detecting flaws in an article to be inspected comprising the steps of:
   (a) directing a substantially level water jet stream against the article;
   (b) imparting relative transverse movement between the article to be inspected and the water jet stream;
   (c) transmitting ultrasonic energy along the water jet stream toward a substantially upright surface of the article to be inspected;
   (d) receiving echoes from the surface of the article and from internal flaws within the article; and
   (e) directing a gas jet stream toward the upright surface of the article to be inspected at a location above and substantially parallel to the water jet stream for thereby deflecting away from the water jet stream water splashing off the surface of the article after impact therewith to prevent the splashing water from descending toward and striking the water jet stream.

12. A method of ultrasonically detecting flaws in an article to be inspected as set forth in claim 11 including the step of:
   (f) recording signals which are representative of the echoes received.

13. A method of ultrasonically detecting flaws in an article to be inspected as set forth in claim 11
   wherein step (a) includes the step of:
   (f) positioning the longitudinal axis of the water jet stream so as to be substantially perpendicular to the surface of the article being inspected; and
   wherein step (e) includes the step of:
   (g) positioning the longitudinal axis of the gas jet stream so as to be substantially perpendicular to the surface of the article being inspected.

14. A method of ultrasonically detecting flaws in an article to be inspected as set forth in claim 11
   wherein the water jet stream of step (a) exhibits laminar flow.

15. A method of ultrasonically detecting flaws in an article to be inspected as set forth in claim 11
   wherein the water jet stream and the gas jet stream are coplanar and vertically aligned.

* * * * *

UNITED STATES PATENT AND TRADEMARK OFFICE
CERTIFICATE OF CORRECTION

PATENT NO. : 5,373,743
DATED : December 20, 1994
INVENTOR(S) : John W. Abrahams

It is certified that error appears in the above-indentified patent and that said Letters Patent is hereby corrected as shown below:

Column 8, line 2, delete "descend"

Signed and Sealed this

Twenty-eight Day of February, 1995

Attest:

BRUCE LEHMAN

*Attesting Officer*    *Commissioner of Patents and Trademarks*